(12) United States Patent
Chowdhury

(10) Patent No.: US 10,646,703 B2
(45) Date of Patent: May 12, 2020

(54) DEVICE FOR CONTAINMENT AND RELEASE OF A TRANSDERMAL DRUG FORMULATION

(71) Applicant: NDM Technologies Limited, Loughborough (GB)

(72) Inventor: Dewan Fazlul Hoque Chowdhury, Loughborough (GB)

(73) Assignee: NDM Technologies Limited, Loughborough (GB)

( * ) Notice: Subject to any disclaimer, the term of this patent is extended or adjusted under 35 U.S.C. 154(b) by 240 days.

(21) Appl. No.: 14/785,277

(22) PCT Filed: Apr. 23, 2014

(86) PCT No.: PCT/GB2014/051265
§ 371 (c)(1),
(2) Date: Oct. 16, 2015

(87) PCT Pub. No.: WO2014/174286
PCT Pub. Date: Oct. 30, 2014

(65) Prior Publication Data
US 2016/0067468 A1 Mar. 10, 2016

(30) Foreign Application Priority Data
Apr. 23, 2013 (GB) .................................. 1307262.4

(51) Int. Cl.
*A61M 37/00* (2006.01)
*A61K 9/00* (2006.01)

(52) U.S. Cl.
CPC .... *A61M 37/0015* (2013.01); *A61M 37/0069* (2013.01); *A61K 9/0021* (2013.01);
(Continued)

(58) Field of Classification Search
CPC .. A61M 5/422; A61M 5/2425; A61M 5/2422; A61M 5/3286; A61M 5/3287;
(Continued)

(56) References Cited

U.S. PATENT DOCUMENTS 6,224,577 B1 * 5/2001 Dedola ............. A61M 5/31513
604/218
6,607,513 B1 * 8/2003 Down ............... A61M 37/0015
604/239

(Continued)

FOREIGN PATENT DOCUMENTS

EP          1 844 763       10/2007
WO          WO 94/22423     10/1994
(Continued)

OTHER PUBLICATIONS

European Patent Office International Search Report dated Jul. 16, 2014, for PCT/GB2014/051265 filed Apr. 23, 2014, Applicant, NDM Technologies Limited (6 pages).

*Primary Examiner* — Kevin C Sirmons
*Assistant Examiner* — Alexandra Lalonde
(74) *Attorney, Agent, or Firm* — McCracken & Gillen LLC

(57) ABSTRACT

This invention relates to a device that uses microneedles to create pores in the skin of a subject and delivers the drug transdermally by inserting it into the pore as a solid or semi-solid mass alongside each needle. The device is sufficiently flexible to allow relative movement of the needle and the drug mass apart from one another. Preferably a chamber holding the drug mass comprises a relatively rigid wall to ensure that the drug remains aligned close to the needle, while an adjacent chamber holding the needle comprises a relatively flexible wall to allow lateral movement of the needle as the drug is inserted alongside it.

15 Claims, 2 Drawing Sheets

(52) U.S. Cl.
    CPC ............... *A61M 2037/0023* (2013.01); *A61M 2037/0038* (2013.01); *A61M 2037/0061* (2013.01)

(58) Field of Classification Search
    CPC .. A61M 5/329; A61M 5/315; A61M 5/31513; A61M 5/34; A61M 2037/0023; A61M 2037/0061; A61M 2037/003; A61M 2037/0038; A61M 2005/341; A61M 2005/31521; A61M 2005/323; A61M 2005/3231; A61M 31/007; A61M 2037/0046; A61K 9/0019; A61K 9/0024; A61K 9/0021; A61K 9/02; A61K 9/025; A61N 5/1027; A61B 10/0035; A61B 17/205
    See application file for complete search history.

(56) References Cited

U.S. PATENT DOCUMENTS

| | | | | |
|---|---|---|---|---|
| 6,659,996 | B1* | 12/2003 | Kaldany | A61B 17/3468 |
| | | | | 604/103.06 |
| 6,939,318 | B2* | 9/2005 | Stenzel | A61B 17/3468 |
| | | | | 604/506 |
| 2007/0243225 | A1* | 10/2007 | McKay | A61K 9/0024 |
| | | | | 424/423 |
| 2010/0211042 | A1* | 8/2010 | Casey | A61M 5/422 |
| | | | | 604/506 |
| 2010/0324530 | A1* | 12/2010 | Hertzog | A61M 5/2053 |
| | | | | 604/506 |
| 2011/0022028 | A1* | 1/2011 | McKay | A61M 37/0069 |
| | | | | 604/511 |
| 2013/0253416 | A1* | 9/2013 | Rotenstreich | A61F 9/0017 |
| | | | | 604/22 |

FOREIGN PATENT DOCUMENTS

| | | |
|---|---|---|
| WO | WO 97/17103 | 5/1997 |
| WO | WO 01/93931 | 12/2001 |
| WO | WO 2004/033021 | 4/2004 |
| WO | WO 2008/134580 | 11/2008 |
| WO | WO 2009/069112 | 6/2009 |
| WO | WO 2010/030965 | 3/2010 |
| WO | WO 2010/109004 | 9/2010 |
| WO | WO 2011/089435 | 7/2011 |
| WO | WO 2012/168691 | 12/2012 |

* cited by examiner

DEVICE FOR CONTAINMENT AND RELEASE OF A TRANSDERMAL DRUG FORMULATION

TECHNICAL FIELD

The invention relates to the field of transdermal delivery of drugs into the body of a patient. In particular, it relates to the composition and structure of the chamber or containment means of a drug formulation that is to be delivered through pores created in the skin.

For the sake of brevity, the term "drug" is used in this specification to refer to any biologically active substance, either on its own or composed as a drug product formulation, that may need to be introduced into the body of a patient to provide a therapeutic, cosmetic or nutritional effect. The patient may be human or a non-human animal. "Transdermal" refers to delivery through the skin of the patient or through any other accessible surface tissue such as the cornea or the inside of the mouth cavity.

BACKGROUND OF THE INVENTION

The main barrier to delivery of drugs through the skin is the stratum corneum, which is a tough outer layer of dead skin cells. Drugs may be delivered using microneedles which may be hollow to provide a channel for delivery of a fluid drug through the stratum corneum or they may be solid and simply coated with the drug for delivery. Some suitable drug formulations can alternatively be formed into solid microneedles made of the drug formulation itself, which can penetrate the stratum corneum and then diffuse into the body. In the case of microneedles the inertia created by fluid flow through the bores of the needles, or the high temperature processing required where drug is encapsulated in polymers, or the large pressures applied to compress the drug itself into needles can affect the stability and integrity of the drug, in particular if the drug is a protein, whereby agglomeration, fragmentation, unfolding, and physical and chemical degradation can result from such processing conditions.

Alternatively, a device comprising solid microneedles may be used to disrupt the stratum corneum and/or to create pores through it in order to enhance its permeability to a drug that is subsequently applied to the surface of the skin, for example in the form of a gel or in a patch. However, because the needles only perforate a small proportion of the surface area of skin being treated, a majority of the subsequently applied drug formulation does not enter the pores but remains on the surface of the skin. Published patent application WO 2012/035334 describes devices for transdermal drug delivery which overcome these impediments by first creating at least one hole in the skin using the needles, followed by the insertion of the drug through the hole/pore that has been created. The patent describes methods and devices for achieving this by first creating the hole in the skin, followed by removal of the needle, and subsequent insertion of the drug through the pore. It also describes the insertion of the drug whilst the needle still remains inside the skin by inserting the drug formulation using a carrier, alongside the needle.

SUMMARY OF THE INVENTION

The invention provides a device for containment or temporary storage of drug to be inserted into the skin of a patient alongside a needle that has been inserted into the skin; the needle remaining partially or completely (i.e., to the desired/maximum depth) inside the skin until after the drug has been delivered.

Specifically, the invention provides a transdermal drug delivery device comprising a first chamber wall that defines a needle chamber for aligning a needle to create a pore in the skin of a patient; and a second chamber wall that defines a drug chamber for aligning a drug mass to be inserted into the pore alongside the needle; characterized in that the device has sufficient flexibility to allow a distance between first chamber wall and the second chamber wall to increase as the drug mass is inserted alongside the needle.

The flexibility of the device may be due to flexure of a connection between the first and second chamber walls or due to flexibility of at least one of the first and second chamber walls. Preferably the first chamber wall is more flexible than the second chamber wall, thereby allowing the needle to move laterally as the drug mass is inserted alongside it. The different flexibility of the chamber walls may arise from their different materials or different structures, or both. Flexibility includes the ability to move, compress or otherwise change shape when a force is applied.

The invention also provides a method of transdermal drug delivery comprising:
aligning a needle in a needle chamber of a drug delivery device;
aligning a drug mass in a drug chamber of the drug delivery device;
placing the device against the skin of a patient;
inserting the needle into the skin to create a pore;
simultaneously or subsequently inserting the drug mass into the pore alongside the needle; and
removing the needle from the skin while leaving the drug mass in place;
characterized in that insertion of the drug mass alongside the needle causes a distance between a first chamber wall of the needle chamber and a second chamber wall of the drug chamber to increase.

The first three steps of this method may be carried out in any order.

The drug is intended to be delivered only to the locations of the previously formed pores, such that a controlled quantity of the drug formulation can be delivered to a precise location and be taken up by the body. There will be minimal wastage of drug left on the surface of the skin and inaccessible to the body. The drug is positioned by the carriers directly inside the pores, beneath the stratum corneum, from where it can be diffused and dispersed through the body like other transdermally delivered treatments.

This is suitable for drug formulations in various states, including solid (powdered or particulate), and semi solid drug formulations. Another major benefit of this method of delivery resides in the minimal processing that the drug would need to be subjected to, thereby avoiding the risk of degrading the active ingredient.

The drug may be in the form of a solid mass, which is shaped to provide a leading edge that allows the drug to locate onto the pore and ease into it. In the case of the drug being inserted along the side of the needle, the drug may be shaped to allow it to ease into the space between the needle wall and the wall of the inner section of skin where the pore has been created. This may be achieved by moulding the drug mass into a shape that has a leading edge that provides a leading tip portion that is narrower than the distal tail portion, though the tip portion in itself would not necessarily be required to be sharp or robust enough to penetrate the skin on its own; this latter point being a key advantage of the versatility of this device with respect to the wide range of drugs that may be delivered using this means. The drug formulations are not required to have the mechanical properties that would allow them to be produced as microneedles, for example, being capable of easy self-insertion into the skin without requiring large forces or without leading to moderate or severe skin trauma during their process of insertion into the skin.

Because the drug is inserted into the skin whilst the needle remains in the skin, either partially or to the maximum desired depth, the drug must be inserted into the skin between the wall of the needle and the inner wall of the pore that has been created in the skin. It has been established that restraining the drug in proximity to the mouth of the pore offers the advantage of the drug being directed into the pore without it being merely compressed onto the surface of the skin adjacent to the pore; this becomes more significant where the drug diameter is equal to or larger than the needle, and where the needle wall facing the drug to be inserted is cylindrical rather than flat for example.

Furthermore it has been established that once the needle has been inserted into the skin, as long as the upper portion of the needle that is not inside the skin is not restrained within a rigid wall/cavity, then the needle will move against the skin in an elastic manner in a direction opposite to the position of insertion of the drug, allowing the drug to squeeze through the space between the wall of the needle and the pore created. It has further been established that securing the drug in a chamber/carrier that has rigid walls either fully or partially around the drug, in particular around the face that is opposite to the needle face, will restrain the movement of the drug in the direction of the resultant force imposed on it by the drug insertion rod as the drug is inserted into the skin through the pore without any possibility of lateral movement of the drug. The restraint leads to forces on the drug from a carrier or insertion rod from above the drug, and forces imposed on the drug from the sidewalls within which the drug is contained prior to delivery. As a result the only direction via which the drug will be able to travel will be in the downward direction, the direction of least resistance, i.e., through the pore alongside the needle that is in the skin. In light of the elasticity of the skin and non-rigid walls within which the needle is secured, the needle will move to accommodate the drug alongside it in the pore.

There may be cases when, as the drug mass is inserted into the pore alongside the needle, it is the drug mass rather than the needle that moves laterally against the skin forming the wall of the pore. This may be the case if the drug mass is much smaller than the needle, or if the needle is flattened to provide a surface against which the drug mass can slide and therefore also presents a large surface area against the wall of the pore. To accommodate such cases, the chamber wall of the drug chamber can also be made flexible; and it is not excluded that it could be more flexible than the chamber wall of the needle chamber.

The elasticity of the skin provides a gripping action against the drug allowing the needle to be removed from the skin, while leaving the drug inside the skin.

THE DRAWINGS

Figure 3:
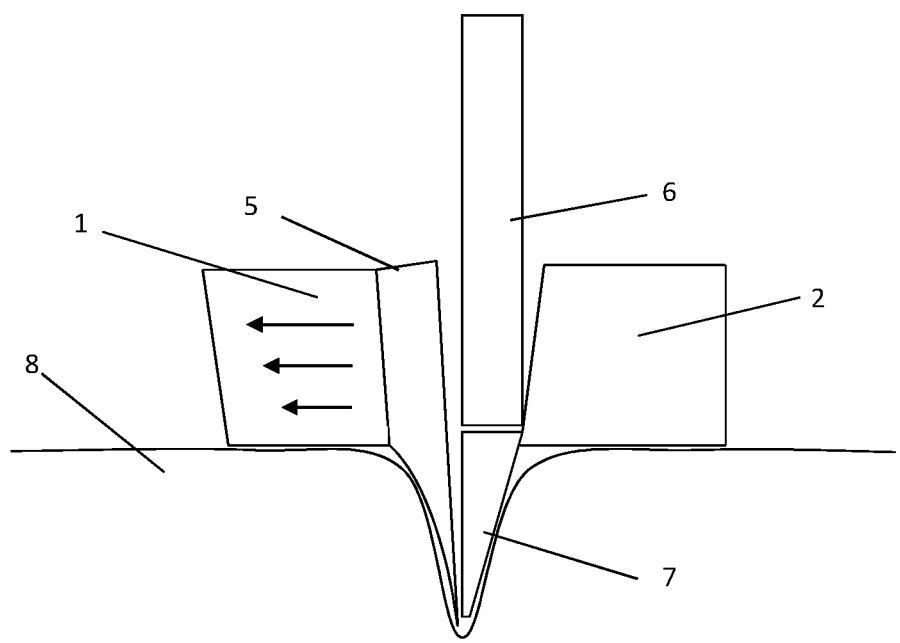
FIG. 3 shows a cross section schematic as shown in FIG. 2, with the device being used to deliver the drug into the skin of a patient.
Figure 4:
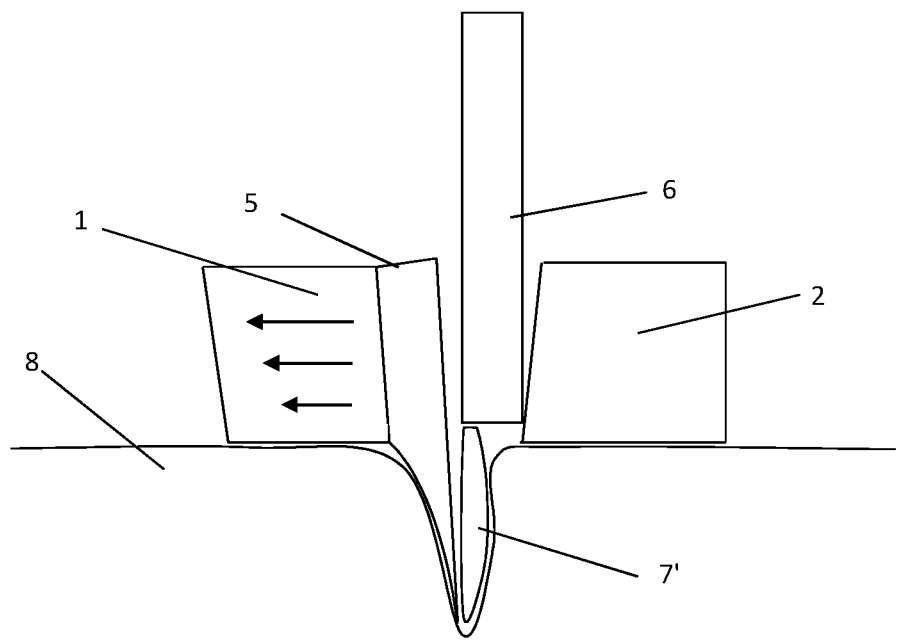

FIG. 4 corresponds to FIG. 3 but shows an alternative shape of drug mass.

Figure 1:
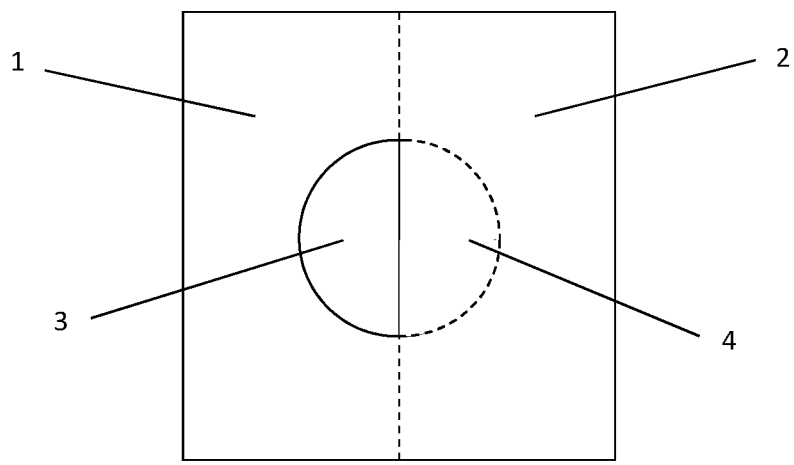
FIG. 1 shows a schematic plan view of a device in accordance with the invention.

In FIG. 1 a device for the containment and release of a transdermal drug formulation is shown. The body of the illustrated device is square in plan, although the overall shape is not of great significance and could take a wide variety of forms. The body of the device comprises a first wall 1 defining a needle chamber 3 and a second wall 2 defining a carrier or containment chamber 4. The first and second walls 1,2 are illustrated as equal halves but that is not essential. The illustrated needle chamber 3 and containment chamber 4 each have a semi-circular cross-section and face one another across a centreline of the device but again it is not essential that they should be equal in size or shape.

Figure 2:
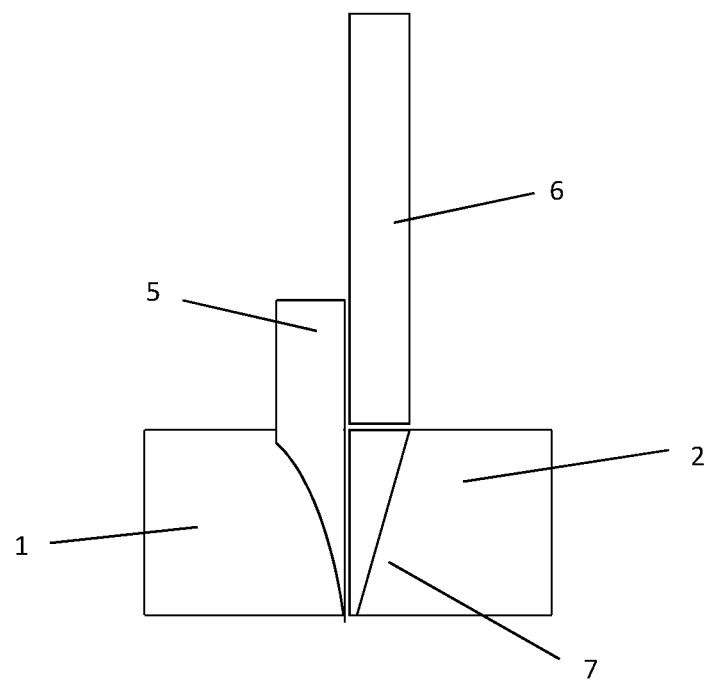
FIG. 2 shows a cross section schematic of the device of FIG. 1.

As shown in FIG. 2, the needle chamber 3 holds and aligns a needle 5 with a sharp tip for forming a pore in the skin of a patient. The containment chamber holds and aligns a solid or semi-solid mass of the drug 7 for delivery into the pore alongside the needle. A solid line between the chambers 3 and 4 is indicated in FIG. 1 to show contact between facing surfaces of the needle 5 and the drug 7, although it is foreseeable that the drug 7 may be entirely encapsulated in its chamber 4 to prevent contact with the needle 5 during storage, in particular where there may be an incompatibility between the needle's material of construction (e.g., metal, ceramic, plastic) and the drug. Such a wall in the region between the drug 7 and needle 5 however would be of minimal thickness, and possibly as little as tens of microns in thickness, constructed of a thin flexible wall of polymer film that in itself may also be biodegradable and may be designed to enter the skin with the drug 7 or to remain intact as the drug passes by it. This small thickness ensures that there is minimal distance between the drug 7 and the adjacent side of the needle because here is located the gap through which the drug 7 must be inserted into the skin. If the drug 7 is too distant from the interface between the needle 5 and the pore in the skin, there is a risk that the drug may instead be forced to spread out on the surface of the non porated region of the skin.

FIG. 2 shows the drug mass 7 as a generally pointed structure, to ensure the leading edge is easily able to access the gap between the needle 5 and the pore in the skin, followed by its insertion into the skin using the insertion rod 6 or other insertion mechanism. This insertion mechanism is not restricted to manually operable methods, and it will be readily appreciated that this can potentially be also achieved using an electromechanical means or pneumatic means where desired, either for rapid insertion or for controlled inserted to a particular depth, though the depth of insertion is also dictated by the distance of travel of the insertion rod 6. The insertion rod 6 may travel relative to the needle 5 after the needle has already been inserted into the skin (by insertion means not illustrated) or may travel with the needle, such that the needle 5 will insert into the skin to a greater overall depth than the insertion rod 6 and drug 7. (It can be seen in FIGS. 2 and 3 that the sharp tip of the needle protrudes below the less sharp tip of the drug mass 7.) The insertion rod 6 may in the latter case be an integral part of the upper part of the body of the needle 5, or it may be permanently attached to the needle, in a fixed position.

The lower surface of the insertion rod 6 that comes into contact with the drug 7 may be shaped to further restrain the lateral movement of the drug 7 during its insertion into the skin, for example a concave region/leading tip on the insertion rod 6. Alternatively, as shown in FIG. 4, the upper portion of the drug 7' may be tapered with a small surface region as a point of contact with the insertion rod 6 such that, following insertion of the drug 7' into the skin 8, the insertion rod 6 may be withdrawn without any potential for drawing the drug 7' out with it, but also providing a means of inserting the drug 7' just below the skin and allowing the skin 8 to relax back over the tapered end of the drug to seal the pore.

In FIG. 3 can be seen the chamber wall 1 of the needle 5 flexing in the opposite direction to the drug 7 as the drug is pushed into the skin 8 using the insertion rod 6. The side wall 2 of the drug chamber is indicated to be slanted, rigid and fixed, whereas the needle chamber wall 1 is shown to be flexing to accommodate the movement of the needle 5, which in turn accommodates the movement of the drug 7 into the pore in the skin 8 alongside the needle 5. It is preferable that the chamber walls 2 holding the drug 7 provide a snug fit such that there is no possibility of lateral motion of the drug 7 away from the needle 5 during the process of insertion, which may have the effect of dampening the force being exerted on to the drug, or redirecting the force from the downwards direction towards the walls.

The walls 1 and 2 of the two chambers 3 and 4 may be produced from the same material, with the same hardness etc., but etched or perforated across the centre such that the wall 1 enclosing the needle 5 is able to flex away from the drug 7 allowing the needle to lean or move laterally upon insertion into the skin. However in order to prevent the lateral movement of the entire chamber 4 holding the drug, the two chamber walls 1 and 2 will be connected at some point along the length of one of the sides or across the base or part of the base to prevent the drug 7 from moving laterally away from the interface between the inserted needle 5 and skin 8. An alternative preferred embodiment would entail the chambers 3 and 4 to be permanently attached across all surfaces between the two chamber walls 1 and 2, but composed of different materials to provide the differential rigidity. For example the needle chamber walls 1 may be produced from a silicone or rubber or other type of material that is non-rigid and may be flexible and elastic; and the drug chamber walls 2 may be produced from a rigid material such as metal or plastic or ceramic. The two may be produced separately and then joined by heat-sealing, chemical adhesive, or by mechanical interlocking. Alternatively they may be moulded in one piece using over-moulding techniques where different components of a single device may be produced from different materials, yet produced as a single injection moulded component. The drug may be loaded either as an individual, discrete, pre-formed entity, or the drug may be cast into the chamber 4 where it is compressed into the requisite shape to fit the chamber, or cast as a liquid or paste that is subsequently dried within the chamber.

The degree of rigidity of the containment chamber 4 in this context may be defined as preventing a level of movement or compression of the walls 2 that causes movement of the drug 7 away from the interface of the inserted needle wall and skin and causes the drug 7 to be predominantly compressed against the adjacent skin when the insertion rod 6 is applied to the drug. It follows that the extent of movement should be no greater than several micrometres, and more specifically less than the width of the leading tip of the drug mass 7. The flexibility of the needle chamber walls 1 may be defined as a degree of flexibility that allows the needle 5 to move laterally to allow the insertion of the drug 7 into the pore along the side of the needle 5 therefore at least equal to or greater than the width of the leading tip of the drug 7.

It will further be readily appreciated that whilst the description refers predominantly to microneedles, this device may utilize needles that are in the tens of microns in diameter through to larger conventional needles that may be several millimetres in diameter. Furthermore the needle may be shaped to be flat or semi-cylindrical, both with a leading narrow tip to provide a tip radius of a few microns, and preferably a wall against which the surface area for drug contact and therefore insertion into the skin is larger than would e the case for a conventional cylindrical shape.

The invention claimed is:

1. A transdermal drug delivery device comprising:
   a first chamber wall that defines a needle chamber for receiving and aligning a needle to create a pore in the skin of a patient, the needle defining a longitudinal direction; and
   a second chamber wall that defines a drug chamber for receiving and aligning a solid drug mass to be inserted into the pore along the side of the needle, wherein the drug mass tapers towards a leading tip;
   wherein the device is flexible to allow a distance between the first chamber wall and the second chamber wall to increase as the drug mass is inserted along the side of the needle, while the needle chamber and the drug chamber remain arranged side by side relative to the longitudinal direction of the needle.

2. The transdermal drug delivery device according to claim 1, wherein the second chamber wall is angled to deflect the drug mass towards the needle as the drug mass is inserted into the pore.

3. The transdermal drug delivery device according to claim 1, wherein the device comprises a flexible connection between the first and second chamber walls.

4. The transdermal drug delivery device according to claim 1, wherein at least one of the first and second chamber walls is flexible.

5. The transdermal delivery device according to claim 4, wherein the first chamber wall and the second chamber wall are made from differently flexible materials.

6. The transdermal delivery device according to claim 4, wherein the first chamber wall and the second chamber wall are formed with differently flexible structures.

7. The transdermal drug delivery device according to claim 5, wherein the first chamber wall is more flexible than the second chamber wall.

8. The transdermal delivery device according to claim 1, wherein the needle chamber and the drug chamber are separated by a thin wall.

9. The transdermal delivery device according to claim 1, wherein the needle chamber and the drug chamber are not separated by a wall.

10. The transdermal delivery device according to claim 1, further comprising the needle supported in the needle chamber and the drug mass supported in the drug chamber.

11. The transdermal delivery device according to claim 10, wherein the drug mass tapers towards a trailing end.

12. A transdermal drug delivery device comprising:
    a first chamber wall that defines a needle chamber for receiving and aligning a needle to create a pore in the skin of a patient, the needle defining a longitudinal direction; and
    a second chamber wall that defines a drug chamber for receiving and aligning a solid drug mass to be inserted into the pore along the side of the needle, wherein the drug mass tapers towards a leading tip, wherein the device is flexible to allow a distance between the first chamber wall and the second chamber wall to increase as the drug mass is inserted along the side of the needle, while the needle chamber and the drug chamber remain arranged side by side relative to the longitudinal direction of the needle, the needle supported in the needle chamber and the drug mass supported in the drug chamber, and wherein the needle comprises a substantially flat face abutting the drug mass.

13. The transdermal delivery device according to claim 10, further comprising an insertion rod for pushing the drug mass into the pore.

14. The transdermal delivery device according to claim 12, wherein the insertion rod is joined to or integral with the needle.

15. A method of transdermal drug delivery comprising:

aligning a needle in a needle chamber of a drug delivery device, the needle defining a longitudinal direction;

aligning a solid drug mass in a drug chamber of the drug delivery device, the needle chamber and the drug chamber being arranged side by side relative to the longitudinal direction of the needle;

placing the device against the skin of a patient;

inserting the needle into the skin to create a pore;

simultaneously or subsequently inserting the drug mass into the pore along the side of the needle; and removing the needle from the skin while leaving the drug mass in place;

wherein insertion of the drug mass along the side of the needle causes a distance between a first chamber wall of the needle chamber and a second chamber wall of the drug chamber to increase, while the needle chamber and the drug chamber remain arranged side by side relative to the longitudinal direction of the needle, wherein, during insertion of the drug mass along the side of the needle, the first chamber wall flexes to allow the needle to move laterally.

* * * * *